United States Patent [19]

Hirano et al.

[11] Patent Number: 5,152,836
[45] Date of Patent: Oct. 6, 1992

[54] HYDRAULIC CALCIUM PHOSPHATE CEMENT COMPOSITION AND CEMENT COMPOSITION CONTAINING HARDENING LIQUID

[75] Inventors: Masahiro Hirano, Saitama; Hiroyasu Takeuchi, Hanno, both of Japan

[73] Assignee: Mitsubishi Materials Corporation, Tokyo, Japan

[21] Appl. No.: 758,664

[22] Filed: Sep. 12, 1991

[30] Foreign Application Priority Data

Sep. 27, 1990 [JP] Japan .................................. 2-255082

[51] Int. Cl.$^5$ ...................... C04B 12/02; C04B 28/34; C09K 3/00; C01B 15/16
[52] U.S. Cl. .................................. 106/690; 106/691; 106/819; 106/35; 423/308; 423/311; 423/315
[58] Field of Search ................. 106/690, 691, 35, 819; 423/308, 309, 311, 315

[56] References Cited

U.S. PATENT DOCUMENTS 4,429,691 2/1984 Niwa et al. ..................... 128/92 C

FOREIGN PATENT DOCUMENTS 64-37445 2/1989 Japan .
244050 2/1990 Japan .
369536 3/1991 Japan .

OTHER PUBLICATIONS

Kadoma, "Calcium Phosphate Hydraulic Cement Composition", May 1989 (Japanese Abstract #01-37445 vol. 13).
Sugihara et al., "Curable Material for Medical & Dental Purposes", Apr. 1990, (Japanese Abstract #02-34172 vol. 14).
Shigeru et al., "Water Soluble Calcium Salt Composition", Sep. 1990, (Japanese Abstract #02-154663 vol. 14).

Primary Examiner—William R. Dixon, Jr.
Assistant Examiner—Michael A. Marcheschi
Attorney, Agent, or Firm—Keil & Weinkauf

[57] ABSTRACT

A hydraulic calcium phosphate cement composition contains as main ingredients powders of calcium tertiary phosphate and calcium secondary phosphate with a molar ratio of Ca/P of 1.400 to 1.498. The calcium tertiary phosphate contains α-type calcium tertiary phosphate and β-type calcium tertiary phosphate. The cement composition may contain a hardening liquid including water.

12 Claims, No Drawings

HYDRAULIC CALCIUM PHOSPHATE CEMENT COMPOSITION AND CEMENT COMPOSITION CONTAINING HARDENING LIQUID

BACKGROUND OF THE INVENTION

This invention relates to a hydraulic calcium phosphate cement composition and a cement composition containing a hardening liquid which are usable as a filler for filling in a defect or hollow portion of bone or a dental root canal portion.

It has been known that a hydraulic calcium phosphate cement composition is useful as a repairing material for teeth and bones of a living body since the calcium phosphate cement composition is converted into compounds resembling main ingredients of teeth and bones due to setting and hardening and is also useful as an absorbing agent for living tissue polymers and for organic substances or inorganic ions harmful in the living body.

In Japanese Laid-open Patent Application No. 59-88351, a hydraulic calcium phosphate cement composition using a hardening liquid containing salts and dilute acids in combination is disclosed. Further, in Japanese Laid-open Patent Application No. 60-253454, a calcium phosphate cement composition using an acid solution containing an unsaturated carboxylic acid polymer is disclosed.

However, the conventional hydraulic calcium phosphate cement compositions have disadvantages that living body is considerably stimulated as the hardening liquid has a strong acidity until the hardening of the cements are completed. Further, even after the cement composition is hardened using the hardening liquid, the unreacted acid is eluted into the living body fluid to thus lower pH value, resulting in stimulating the living body.

To solve these problems, therefore, a hydraulic calcium phosphate cement composition hardenable with water is developed (for example, "FC REPORT", vol. 6 (1988), pp. 475~480 "Hydraulic Apatite as Bioceramics"). More in detail, proposed by Japanese Laid-open Patent Application No. 64-37445 is a hydraulic calcium phosphate cement composition hardenable by mixing and kneading with only water at 37° C. for about 10 minutes. Since this cement composition has almost neutral pH value, such composition has less stimulation to the living body, thus eliminating the disadvantages associated with the conventional hydraulic calcium phosphate compositions.

However, this cement composition has another problem that there is extremely high risk of deterioration and degradation in the living body since the cement composition contains $\alpha$-type calcium tertiary phosphate and calcium secondary phosphate dihydrate with a molar ratio of Ca/P of 1.20 to 1.47 so that when the cement composition is left in water for a long time, it is extremely degraded, leading to destruction in the living body.

SUMMARY OF THE INVENTION

An object of the present invention is to provide a hydraulic calcium phosphate cement composition and a cement composition containing a hardening liquid which are rapidly hardened at almost neutral pH value to obtain a hardened cement composition and which give a hardened body excellent in compatibility with living tissues and resistance to the degradation for a long period of time.

The above and other objects of the invention will become apparent from the following description.

In accordance with the present invention, provided is a hydraulic calcium phosphate cement composition comprising as main ingredients powders of calcium tertiary phosphate and calcium secondary phosphate with a molar ratio of Ca/P ranging from 1.400 to 1.498, the calcium tertiary phosphate containing $\alpha$-type calcium tertiary phosphate and $\beta$-type calcium tertiary phosphate.

Further, according to the present invention, provided is a cement composition containing a hardening liquid comprising the aforementioned hydraulic calcium phosphate cement composition and a hardening liquid containing water.

PREFERRED EMBODIMENTS OF THE INVENTION

The present invention will be explained in more detail hereinbelow.

A hydraulic calcium phosphate cement composition of the present invention contains as main ingredients calcium secondary phosphate and specific calcium tertiary phosphate in a specific molar ratio of Ca/P.

Calcium tertiary phosphate employed as the powders in the hydraulic calcium phosphate cement composition of the present invention is a mixture containing $\alpha$-type calcium tertiary phosphate and $\beta$-type calcium tertiary phosphate. When octacalcium phosphate is formed and hardened by reacting $\alpha$-type calcium tertiary phosphate with calcium secondary phosphate, $\alpha$-type calcium tertiary phosphate reacts to allow a hardened cement composition to exhibit a strong initial strength thereof. $\beta$-type calcium tertiary phosphate having a far retarded reaction velocity as compared with that of $\alpha$-type calcium tertiary phosphate gradually reacts to allow the hardened cement composition to exhibit an increasing strength thereof with lapse of time. Thus, using the mixture of the $\alpha$-type calcium tertiary phosphate and $\beta$-type calcium tertiary posphate, the deterioration in strength of the hardened cement composition is capable of being prevented.

It is preferable that $\alpha$-type calcium tertiary phosphate and $\beta$-type calcium tertiary phosphate be mixed in a mixing ratio by weight ranging from 97:3 to 50:50. If the mixing ratio of $\beta$-type calcium tertiary phosphate is less than 3, the deterioration of strength may not be prevented. If the ratio is more than 50, the initial strength may become lower. Thus, the aforementioned mixing ratio is preferable.

To prepare the $\alpha$-type calcium tertiary phosphate and the $\beta$-type calcium tertiary phosphate, for example a mixture of an equivalent mole of calcium pyrophosphate and calcium carbonate may be reacted in the solid phase by a dry process. In the process, to obtain $\alpha$-type calcium tertiary phosphate, a sintering temperature may preferably be not less than 1200° C. and to obtain $\beta$-type tertiary calcium phosphate, the sintering temperature may preferably be from 900° C. to 1100° C. Alternatively, a wet process may be employed in which after each of tertiary calcium phosphate slurries synthesized by adding phosphoric acid dropwise to slaked lime is dried, $\alpha$-type tertiary calcium phosphate and $\beta$-type tertiary calcium phosphate may be sintered in the above respective temperature ranges.

Calcium tertiary phosphate synthesized by the wet process in comparison with the dry process has higher hydration activity, a shorter hardening time and a higher strength of the hardened cement composition so that the wet process is preferable. In such case, both α-type calcium tertiary phosphate and β-type calcium tertiary phosphate may be synthesized by the wet process. To obtain the aforementioned effects, however, it is preferable that at least α-type calcium tertiary phosphate be synthesized by the wet process.

As calcium secondary phosphate used as the powders of the present invention, it is not specially limited but a commercially available calcium secondary phosphate dihydride may preferably be used.

Further, the molar ratio of Ca/P of from 1.400 to 1.498 is needed when calcium tertiary phosphate and calcium secondary phosphate are mixed. If the molar ratio of Ca/P is less than 1.400, unreacted calcium secondary phosphate remains in a large amount after mixing and kneading so that the strength of the hardened cement composition becomes lower. When the molar ratio of Ca/P is more than 1.498, it takes a long period of time to be hardened.

Furthermore, to enhance the compatibility with living tissues and improve the hardening properties of the hydraulic calcium phosphate cement composition of the present invention, ceramics powders such as calcium quaternary phosphate, hydroxyapatite or alumina may be added to the powders containing calcium tertiary phosphate and calcium secondary phosphate.

According to the present invention, the hardening liquid containing water may be added to the hydraulic calcium phosphate cement composition to obtain a cement composition containing the hardening liquid. As the hardening liquid containing water, only water may suffice but a water soluble sodium salt may be contained to shorten the hardening time and improve the strength of the cement composition. As the water soluble sodium salt, sodium succinate, sodium lactate, sodium acetate and sodium chloride and the like are enumerated. They may be employed singly or as a mixture. It is particularly preferable to use sodium succinate and sodium lactate since they promote remarkable hardening and accelerate convertion into apatite in the living body. And most preferably, sodium succinate may be employed since it may increase the strength of the hardened cement composition in comparison with the cases where the other water soluble sodium salts or no salts are added.

Hardening effects of the water soluble sodium salt increases with an added amount increasing and reaches a saturation point at the specific amount. Since the added amounts of the water soluble sodium salts vary depending on the mixing ratio of α-type calcium tertiary phosphate, β-type calcium tertiary phosphate and calcium secondary phosphate and the kinds of the salts, the added amount is not specifically limited. However, it is preferable that the added amount be not more than 30 wt % based on the total hardening liquid. For example, when the hardening liquid containing 20 wt % of sodium succinate is added to the hydraulic calcium phosphate cement composition containing the mixed powders of calcium tertiary phosphate and calcium secondary phosphate with a molar ratio of Ca/P of 1.48 in which calcium tertiary phosphate is synthesized by the wet process and contains α-type calcium tertiary phosphate and β-type calcium tertiary phosphate with the mixing ratio of 80:20 by weight, the cement composition may be hardened for about 10 minutes.

If needed, to further improve handling properties upon mixing and kneading and wettability of the cement composition, a water soluble polymer may be added to the hardening liquid containing water. As the water soluble polymers, polysaccharides and polymer surfactants may preferably be employed. Specific examples of the polysaccharides may be enumerated by chitin, chitosan, soluble starch, glycogen, gum arabi, alginic acid, hyaluronic acid, chondroitin sulfuric acid and their salts. And specific examples of the polymer surfactants may be enumerated by polypropylene glycol, polyethylene glycol, polyvinyl alcohol, methyl cellulose, carboxymethyl cellulose, hydroxypropylmethyl cellulose, etc. They may be used singly or as a mixture thereof. A content of the water soluble polymer may be used in a range from the minimum amount to achieve the aforementioned objects to the maximum amount not to injure the handling properties by an increased viscosity.

The cement composition containing the hardening liquid of the present invention is mixed and kneaded to obtain the desired hardened cement composition. In this case, it is preferable that the hydraulic calcium phosphate cement composition and the hardening liquid containing water be mixed in the mixing ratio of 1.0 to 2.5:1.0 by weight. If the mixing ratio of the hydraulic calcium phosphate cement composition is less than 1.0, it takes a long time to be hardened and the strength becomes lower. If the ratio is more than 2.5, the handling properties upon mixing and kneading become difficult since the mixture is hardened too much.

The hydraulic calcium phosphate cement composition and the cement composition containing the hardening liquid of the present invention have advantages that the cement composition may be hardened at pH of the neutral zone and in a practical time period, the hardened cement composition has high strength so as not to deteriorate the strength for a long period of time as well as superior compatibility with living tissues.

When at least α-type calcium tertiary phosphate synthesized by the wet process is contained as calcium tertiary phosphate, the hardened cement composition having shorter hardening time and higher strength may be obtained.

Therefore, the hydraulic calcium phosphate cement composition and the cement composition containing the hardening liquid of the present invention are usable as a filler for filling in a defect or hollow portion of bone or a dental root canal portion.

EXAMPLES OF THE INVENTION

The present invention will be explained in more detail with reference to examples and comparative examples thereof. However, it is to be noted hereby that the invention should not be limited to the following examples.

EXAMPLE 1

α-type calcium tertiary phosphate synthesized from slaked lime and phosphoric acid by a wet process and β-type calcium tertiary phosphate synthesized from calcium pyrophosphate and calcium carbonate by a dry process were mixed to prepare calcium tertiary phosphate having a mixing ratio of 80:20 by weight. Then, the calcium tertiary phosphate thus prepared and calcium secondary phosphate (manufactured by WAKO PURE CHEMICAL INDUSTRIES, LTD.) were mixed to prepare hydraulic calcium phosphate cement compositions respectively having molar ratios of Ca/P of 1.40, 1.45, 1.48 and 1.498. To 200 weight parts of each of the hydraulic calcium cement compositions thus obtained, 100 weight parts of a hardening liquid or water were added and the mass was mixed and kneaded to obtain a hardened cement composition. The hardening time of the mixture was measured generally in accordance with JIS T6604. Further, after leaving the hardened cement compositions in artificial body fluid for one day, the hardened cement pieces (diameter 7 mm, length 14 mm) were taken out of the fluid and measured each compressive strength thereof under the wet condition under the compression of accelerated rate of 1 mm/min by using Instron Universal Tester "Model 1125". The measured results are shown in Table 1.

COMPARATIVE EXAMPLE 1

Following the procedures of Example 1, calcium tertiary phosphate obtained in accordance with Example 1 and calcium secondary phosphate dihydrate were mixed to prepare hydraulic calcium phosphate cement compositions respectively having the molar ratios of Ca/P of 1.35 and 1.499. Then, according to Example 1, each of the cement compositions was hardened and each hardening time and compressive strength were measured. The results are shown in Table 1.

phate were changed to have various compositional ratios as shown in Table 2. The aforementioned calcium tertiary phosphate and calcium secondary phosphate were mixed to prepare hydraulic calcium phosphate cement compositions having the molar ratios of Ca/P of 1.48. Then, to 100 weight parts of each of the cement compositions obtained, 60 weight parts of a 20 wt % aqueous solution of sodium succinate hexahydrate (manufactured by WAKO PURE CHEMICAL INDUSTRIES, LTD.) were added as a hardening liquid and the mass was mixed and kneaded. The hardening time of each mixture was measured generally in accordance with JIS T6604. Further, according to Example 1, the compressive strengths of the hardened cement pieces were measured after leaving the pieces in the artificial body fluid for one day, three days, seven days, thirty days, sixty days and ninety days, respectively.

The results are shown in Table 2.

COMPARATIVE EXAMPLE 2

Using calcium tertiary phosphate not containing $\beta$-type calcium tertiary phosphate, the hydraulic calcium phosphate cement compositions were prepared and hardened and the hardening time and the compressive strength of the pieces obtained were measured in accordance with Example 3.

The results are shown in Table 2.

TABLE 2

|  |  | Compositional ratio of $\beta$-type calcium tertiary phosphate | | | | | |
|---|---|---|---|---|---|---|---|
|  |  | Comp. Ex. 2 | Example 3 | | | | |
|  |  | 0% | 3% | 10% | 20% | 40% | 50% |
| Hardening time (min.) |  | 8 | 9 | 9 | 10 | 12 | 15 |
| Compressive | 1 day | 351 | 322 | 310 | 296 | 222 | 205 |
| strength | 3 days | 292 | 288 | 277 | 218 | 200 | 166 |
| (kg/cm$^2$) | 7 days | 239 | 234 | 240 | 214 | 209 | 187 |
|  | 30 days | 219 | 250 | 241 | 263 | 215 | 210 |
|  | 60 days | 204 | 276 | 282 | 307 | 264 | 245 |
|  | 90 days | 186 | 290 | 305 | 295 | 319 | 288 |
| Presence or absence of degradation |  | Found | None | None | None | None | None |

EXAMPLE 2

The procedures of Example 1 were repeated except that α-type calcium tertiary phosphate was synthesized from calcium pyrophosphate and calcium carbonate by a dry process. Then, similarly to Example 1, hydraulic calcium phosphate cement compositions were prepared and hardened and the hardening time and the compressive strength thereof were measured.

The results are shown in Table 1.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

TABLE 1

|  | Ex. 1 | | | | Comparative Ex. 1 | | Ex. 2 | | | |
|---|---|---|---|---|---|---|---|---|---|---|
| Molar ratio of Ca/P | 1.40 | 1.45 | 1.48 | 1.498 | 1.35 | 1.488 | 1.40 | 1.45 | 1.48 | 1.498 |
| Hardening time (min.) | 12 | 12 | 35 | 60 | 12 | 110 | 15 | 15 | 50 | 80 |
| Compressive strength (kg/cm$^2$) | 200 | 225 | 255 | 280 | 130 | 270 | 170 | 205 | 235 | 250 |

EXAMPLE 3

With respect to calcium tertiary phosphate containing α-type calcium tertiary phosphate and β-type calcium tertiary phosphate, which were both synthesized from slaked lime and phosphoric acid by the wet process, the contents of the β-type calcium tertiary phos- 1. A hydraulic calcium phosphate cement composition comprising as main ingredients powders of calcium tertiary phosphate and calcium secondary phosphate with a molar ratio of Ca/P of 1.400 to 1.498, said calcium tertiary phosphate containing α-type calcium tertiary phosphate and β-type calcium tertiary phosphate.

2. The hydraulic calcium phosphate cement composition of claim 1, in which said α-type calcium tertiary phosphate and said β-type calcium tertiary phosphate are mixed in a mixing ratio of 97:3 to 50:50 by weight.

3. The hydraulic calcium phosphate cement composition of claim 1, in which at least α-type calcium tertiary phosphate contained in said calcium tertiary phosphate is synthesized by a wet process.

4. The hydraulic calcium phosphate cement composition of claim 1, in which said α-type calcium tertiary phosphate and said β-type calcium tertiary phosphate are synthesized by a wet process.

5. The hydraulic calcium phosphate cement composition of claim 1, in which said α-type calcium tertiary phosphate is synthesized at a sintering temperature not less than 1200° C.

6. The hydraulic calcium phosphate cement composition of claim 1, in which said β-type calcium tertiary phosphate is synthesized at a sintering temperature from 900° C. to 7. The hydraulic calcium phosphate cement composition of claim 1 further comprising ceramics powders selected from the group consisting of calcium quarternary phosphate, hydroxyapatite, alumina and mixtures thereof.

8. A cement composition containing a hardening liquid comprising the hydraulic calcium phosphate cement composition of claim 1 and a hardening liquid containing water, said hydraulic calcium phosphate cement composition and said hardening liquid containing water being mixed in a mixing ratio of 1.0 to 2.5:1.0 by weight.

9. The cement composition containing a hardening liquid of claim 8 further comprising a water soluble sodium salt selected from the group consisting of sodium succinate, sodium lactate, sodium acetate, sodium chloride and mixtures thereof, an added amount of said water soluble sodium salt being not more than 30 wt % based on the total hardening liquid containing water.

10. The cement composition containing a hardening liquid of claim 8, in which said hardening liquid containing water further contains a water soluble polymer selected from the group consisting of polysaccharides, a polymer surfactant and mixtures thereof.

11. The cement composition containing a hardening liquid of claim 10, in which said polysaccharides are selected from the group consisting of chitin, chitosan, soluble starch, glycogen, gum arabi, alginic acid, hyaluronic acid, chondroitin sulfuric acid and a salt thereof and mixtures thereof.

12. The cement composition containing a hardening liquid of claim 10, in which said polymer surfactant is selected from the group consisting of polypropylene glycol, polyethylene glycol, polyvinyl alcohol, methyl cellulose, carboxymethyl cellulose, hydroxypropylmethyl cellulose and mixtures thereof.

* * * * *

UNITED STATES PATENT AND TRADEMARK OFFICE
CERTIFICATE OF CORRECTION

PATENT NO. : 5,152,836
DATED : October 6, 1992
INVENTOR(S) : HIRANO et al.

It is certified that error appears in the above-identified patent and that said Letters Patent is hereby corrected as shown below:

<u>In claim 6, col. 7, line 20</u>

"900°C to" should read --900°C to 1100°C--

Signed and Sealed this

Fifth Day of October, 1993

Attest:

BRUCE LEHMAN

*Attesting Officer*  *Commissioner of Patents and Trademarks*